United States Patent [19]
Button

[11] Patent Number: 6,125,858
[45] Date of Patent: Oct. 3, 2000

[54] WRITING INSTRUMENT DENTAL DEVICE ATTACHMENT

[76] Inventor: Patsy J. Button, 295 Balmoral Drive, Brampton, Ontario, Canada, L6T 1V5

[21] Appl. No.: 09/329,179

[22] Filed: Jun. 10, 1999

[51] Int. Cl.[7] .............................. A61C 15/00; A61C 3/00; B43K 29/00
[52] U.S. Cl. ..................... 132/321; 132/329; 401/195; 433/141
[58] Field of Search ..................... 132/321, 329, 132/323, 324, 325, 328, 308, 309, 310; 401/195, 52; 433/141, 142, 143; 601/139

[56] References Cited

U.S. PATENT DOCUMENTS

| | | | |
|---|---|---|---|
| D. 310,308 | 9/1990 | Wolsey | D4/100 |
| 4,800,905 | 1/1989 | Stuart | 132/321 |
| 5,009,535 | 4/1991 | Oilar | 401/195 |
| 5,071,348 | 12/1991 | Woog | 132/308 |
| 5,090,907 | 2/1992 | Hewitt et al. | 433/141 |
| 5,117,848 | 6/1992 | Huang | 132/308 |
| 5,119,803 | 6/1992 | Fishman | 433/80 |
| 5,161,971 | 11/1992 | Neiner et al. | 433/141 |
| 5,323,795 | 6/1994 | Berens | 132/309 |
| 5,348,028 | 9/1994 | Gustavel | 132/309 |
| 5,642,741 | 7/1997 | Choi | 132/321 |
| 5,865,552 | 2/1999 | Manno | 401/195 |
| 5,906,213 | 5/1999 | Diffendal | 132/309 |

*Primary Examiner*—John J. Wilson
*Assistant Examiner*—Robyn Kieu Doan

[57] ABSTRACT

A writing instrument dental device attachment for mounting to an end of a writing instrument to permit a user to perform oral hygiene activities therewith. The writing instrument dental device attachment includes a tubular attachment sleeve with an open proximal end for receiving therein one end of a writing instrument. At least one dental tool is also provided having an elongate shaft portion and a head portion at a first end of the shaft portion of the dental tool. A distal end of the attachment sleeve receives therein a second end of the dental tool to attach the dental tool to the attachment sleeve.

17 Claims, 3 Drawing Sheets

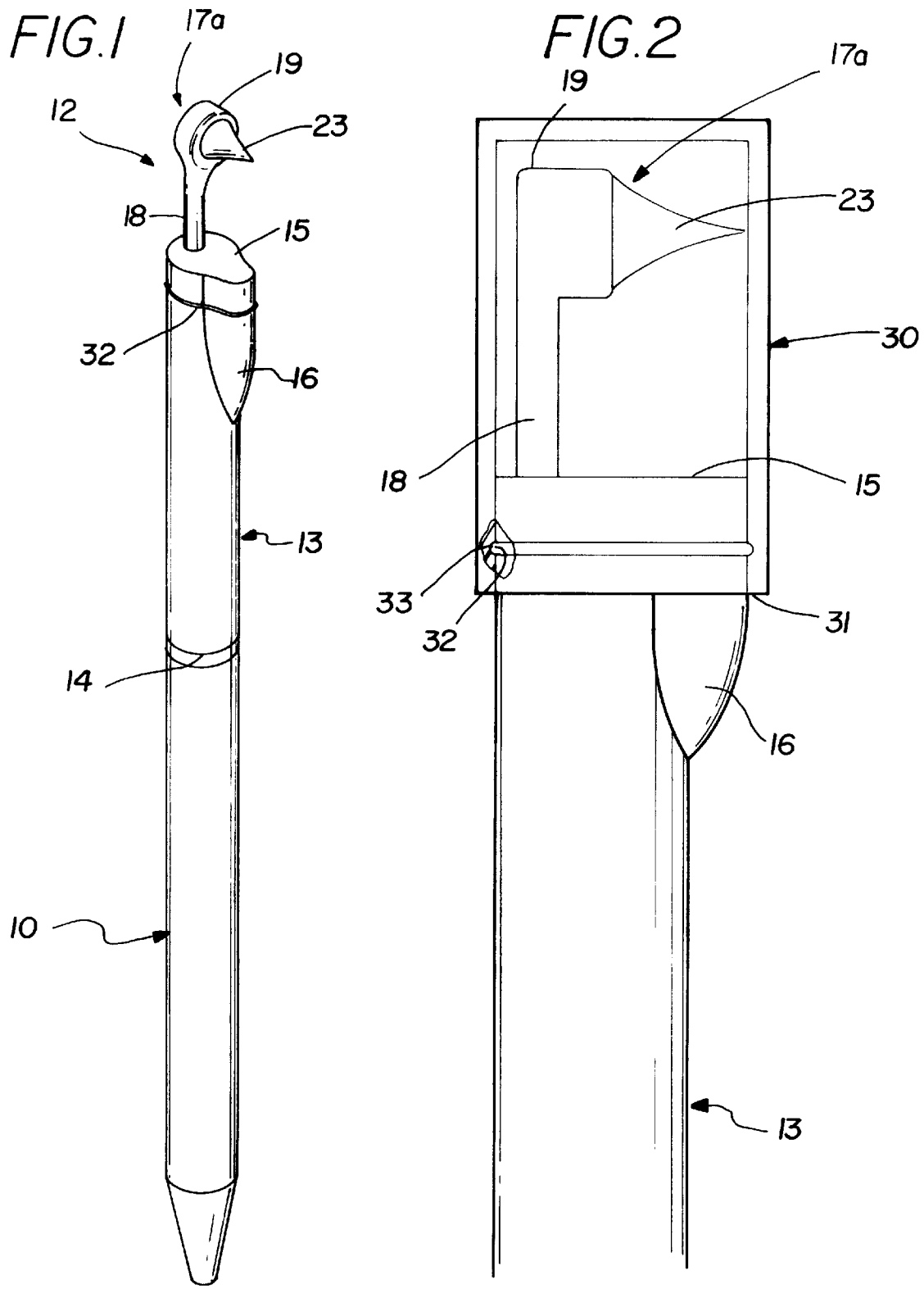

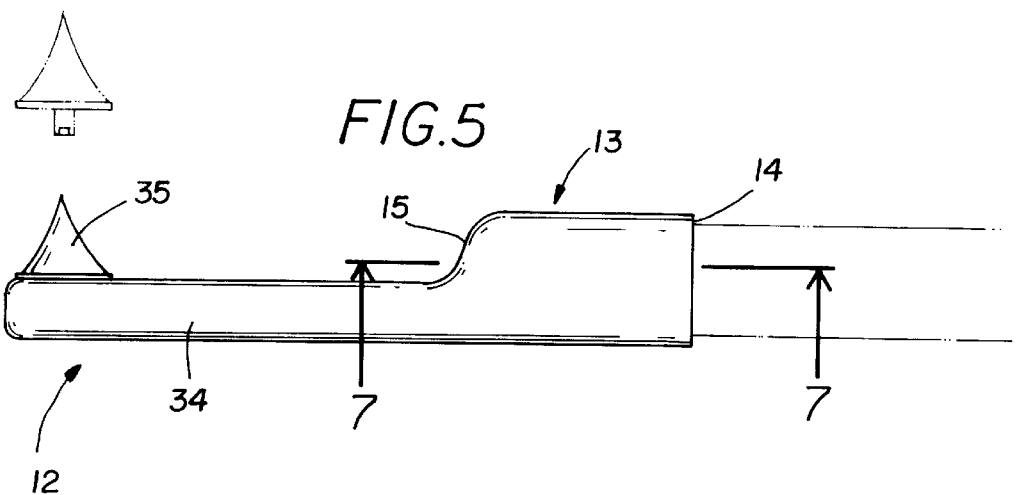
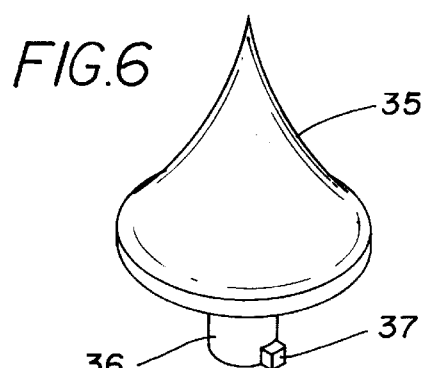
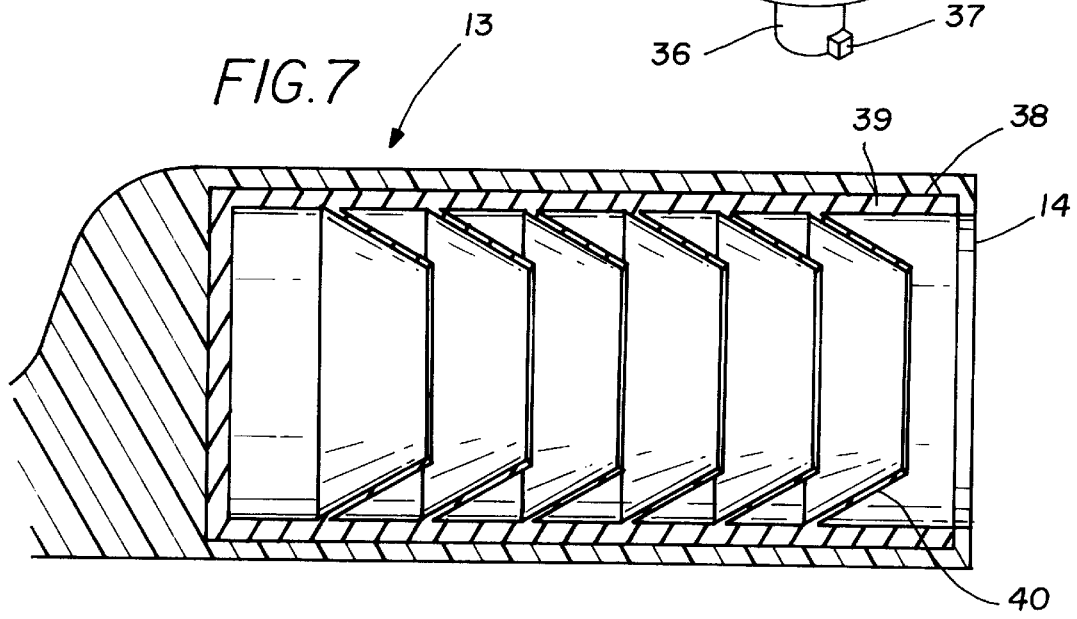

WRITING INSTRUMENT DENTAL DEVICE ATTACHMENT

BACKGROUND OF THE INVENTION

1. Field of the Invention

The present invention relates to dental device attachments for writing instruments and more particularly pertains to a new writing instrument dental device attachment for mounting to an end of a writing instrument to permit a user to perform oral hygiene activities therewith.

2. Description of the Prior Art

The use of dental device attachments for writing instruments is known in the prior art. More specifically, dental device attachments for writing instruments heretofore devised and utilized are known to consist basically of familiar, expected and obvious structural configurations, notwithstanding the myriad of designs encompassed by the crowded prior art which have been developed for the fulfillment of countless objectives and requirements.

Known prior art includes U.S. Pat. No. 3,749,503; U.S. Pat. No. 4,919,156; U.S. Pat. No. 4,919,155; U.S. Pat. No. 4,653,480; U.S. Pat. No. 5,205,302; U.S. Pat. No. 4,326,548; and U.S. Pat. No. Des. 310,308.

While these devices fulfill their respective, particular objectives and requirements, the aforementioned patents do not disclose a new writing instrument dental device attachment. The inventive device includes a tubular attachment sleeve with an open proximal end for receiving therein one end of a writing instrument. At least one dental tool is also provided having an elongate shaft portion and a head portion at a first end of the shaft portion of the dental tool. A distal end of the attachment sleeve receives therein a second end of the dental tool to attach the dental tool to the attachment sleeve.

In these respects, the writing instrument dental device attachment according to the present invention substantially departs from the conventional concepts and designs of the prior art, and in so doing provides an apparatus primarily developed for the purpose of mounting to an end of a writing instrument to permit a user to perform oral hygiene activities therewith.

SUMMARY OF THE INVENTION

In view of the foregoing disadvantages inherent in the known types of dental device attachments for writing instruments now present in the prior art, the present invention provides a new writing instrument dental device attachment construction wherein the same can be utilized for mounting to an end of a writing instrument to permit a user to perform oral hygiene activities therewith.

The general purpose of the present invention, which will be described subsequently in greater detail, is to provide a new writing instrument dental device attachment apparatus and method which has many of the advantages of the dental device attachments for writing instruments mentioned heretofore and many novel features that result in a new writing instrument dental device attachment which is not anticipated, rendered obvious, suggested, or even implied by any of the prior art dental device attachments for writing instruments, either alone or in any combination thereof.

To attain this, the present invention generally comprises a tubular attachment sleeve with an open proximal end for receiving therein one end of a writing instrument. At least one dental tool is also provided having an elongate shaft portion and a head portion at a first end of the shaft portion of the dental tool. A distal end of the attachment sleeve receives therein a second end of the dental tool to attach the dental tool to the attachment sleeve.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new writing instrument dental device attachment apparatus and method which has many of the advantages of the dental device attachments for writing instruments mentioned heretofore and many novel features that result in a new writing instrument dental device attachment which is not anticipated, rendered obvious, suggested, or even implied by any of the prior art dental device attachments for writing instruments, either alone or in any combination thereof.

It is another object of the present invention to provide a new writing instrument dental device attachment which may be easily and efficiently manufactured and marketed.

It is a further object of the present invention to provide a new writing instrument dental device attachment which is of a durable and reliable construction.

An even further object of the present invention is to provide a new writing instrument dental device attachment which is susceptible of a low cost of manufacture with regard to both materials and labor, and which accordingly is then susceptible of low prices of sale to the consuming public, thereby making such writing instrument dental device attachment economically available to the buying public.

Still yet another object of the present invention is to provide a new writing instrument dental device attachment which provides in the apparatuses and methods of the prior art some of the advantages thereof, while simultaneously overcoming some of the disadvantages normally associated therewith.

Still another object of the present invention is to provide a new writing instrument dental device attachment for mounting to an end of a writing instrument to permit a user to perform oral hygiene activities therewith.

Yet another object of the present invention is to provide a new writing instrument dental device attachment which includes a tubular attachment sleeve with an open proximal end for receiving therein one end of a writing instrument. At least one dental tool is also provided having an elongate shaft portion and a head portion at a first end of the shaft portion of the dental tool. A distal end of the attachment sleeve receives therein a second end of the dental tool to attach the dental tool to the attachment sleeve.

Still yet another object of the present invention is to provide a new writing instrument dental device attachment that may also be provided with additional interchangeable dental device attachments.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be made to the accompanying drawings and descriptive matter in which there are illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 1 is a schematic perspective view of an embodiment of the present invention.

FIG. 2 is a schematic enlarged side view of an embodiment of the present invention with a cap on the distal end of the attachment sleeve.

FIG. 5 is a schematic side view of another embodiment of the present invention.

FIG. 6 is a schematic perspective view of the pick of the embodiment illustrated in FIG. 5.

FIG. 7 is a schematic cross sectional view taken from line 7—7 of FIG. 5.

DESCRIPTION OF THE PREFERRED EMBODIMENT

Figure 3:
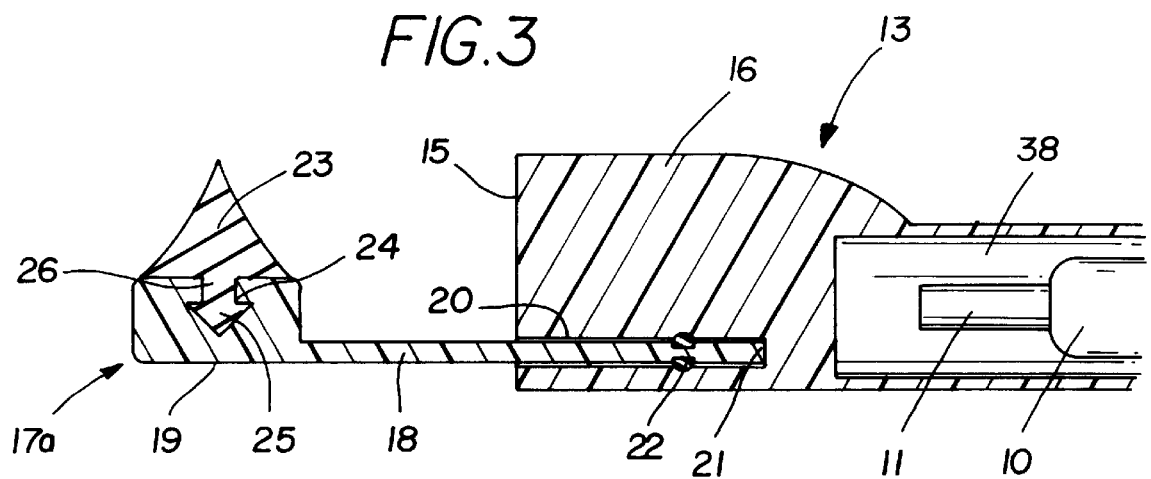
FIG. 3 is a schematic cross sectional view of the embodiment of the present invention illustrated FIG. 1.

With reference now to the drawings, and in particular to FIGS. 1 through 7 thereof, a new writing instrument dental device attachment embodying the principles and concepts of the present invention will be described.

As best illustrated in FIGS. 1 through 7, the writing instrument dental device attachment generally comprises a tubular attachment sleeve with an open proximal end for receiving therein one end of a writing instrument. At least one dental tool is also provided having an elongate shaft portion and a head portion at a first end of the shaft portion of the dental tool. A distal end of the attachment sleeve receives therein a second end of the dental tool to attach the dental tool to the attachment sleeve.

In closer detail, the writing instrument dental device attachment is a system which includes writing instrument 10 having at least one end. In one embodiment, the writing instrument may comprise a retractable ink pen with a depressible retraction actuating button 11 outwardly extending from the one end of the writing instrument.

The system also includes a dental hygiene attachment 12 which comprises a tubular attachment sleeve 13 having an open proximal end 14 and a closed distal end 15. The proximal end of the attachment sleeve receives therein the one end of the writing instrument to attach the attachment sleeve to the one end of the writing instrument.

The distal end of the attachment sleeve may optionally have a generally oblong finger extent 16 thereadjacent for providing a location for a user to place a finger or thumb thereagainst when holding the writing instrument while using and manipulating the attachment.

The system also includes at least one dental tool 17a,17b, 17c having an elongate shaft portion 18 and a head portion 19 at a first end of the shaft portion of the dental tool.

The distal end of the attachment sleeve has a bore 20 therein. The shaft portion of the dental tool has a second end 21 opposite the first end of the dental tool. The second end of the shaft portion of the dental tool is inserted into the bore of the distal end of attachment sleeve.

Optionally, the shaft portion of the dental tool may have a resiliently deformable annular retaining ring 22 therearound positioned towards the second end of the shaft portion of the dental tool. The retaining ring of the shaft portion of the dental tool is inserted into the bore of the distal end of the attachment sleeve, the retaining ring is deformed in the bore to hold the second end of the shaft portion in the bore.

With reference to FIGS. 1, 2, and 3, the head portion of a first of the dental tools 17a may comprise a generally conical-shaped resilient deformable pick 23 has an outwardly extending point designed for insertion between the teeth and gums of a user. In one embodiment, the pick of the first dental tool may have an axis extending substantially perpendicular to the shaft portion of the first dental tool.

Also, as illustrated in FIG. 3, the head portion of the first dental tool may have a bore therein receiving a resiliently deformable attachment extent 24 of the pick of the first dental tool to detachably attach the pick to the head portion of the first dental tool to permit replacement of the pick when worn out or damaged. In such an embodiment, the attachment extent of the first dental tool may even have a generally conical outer portion 25 and a generally cylindrical inner portion 26. In such an embodiment, the bore of the head portion of the first dental tool should have a shape complementary to the portions of the attachment extent.

Figure 4:
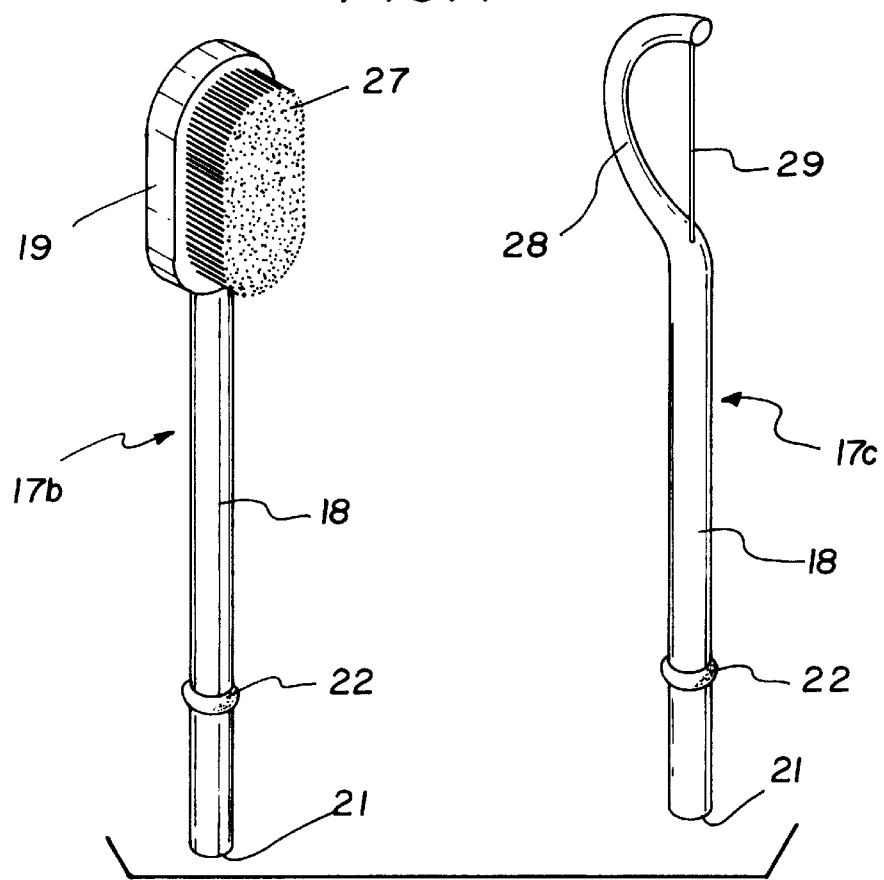
FIG. 4 is a schematic perspective view of the second and third dental tools.

With reference to FIG. 4, the head portion of a second of the dental tools 17b may comprise a toothbrush having a plurality of outwardly extending flexible bristles 27 for brushing a user's teeth therewith.

Also with reference to FIG. 4, the head portion of a third of the dental tools 17c may comprise a generally C-shaped arcuate floss holder 28 and a length of dental floss 29 extending between opposing ends of the floss holder. In one embodiment of the third dental tool, the floss holder and the shaft portion of the third dental tool may lie in a common plane with one another.

A cap 30 may be mounted to the distal end of the attachment sleeve to cover the dental tool therein as shown in FIG. 2. In such an embodiment, the cap may comprise a translucent and/or transparent material. The cap has an open end 31 which receives the distal end of the attachment sleeve.

In one embodiment, the attachment sleeve may have a resilient attachment ridge 32 therearound adjacent the distal end of the attachment sleeve. In this embodiment, the cap may have an annular inner retaining groove 33 adjacent the open end of the cap. The inner retaining groove receives therein the attachment ridge of the attachment sleeve to hold the cap on the distal end of the attachment sleeve.

FIGS. 5, 6, and 7 illustrate an optional embodiment of the attachment sleeve. Features of this embodiment may also be included in the embodiment of the attachment sleeve illustrated in FIGS. 1 and 3. In such an embodiment, the distal end of the attachment sleeve has an elongate shaft 34 outwardly extending therefrom which terminates at a free end.

A resiliently deformable generally conical-shaped pick 35 is coupled to the shaft of the attachment sleeve adjacent the free end of the shaft. As illustrated in FIG. 6, the pick may have a generally cylindrical attachment prong 36 inserted into a hole in the shaft of the attachment sleeve adjacent the free end of the shaft of the attachment sleeve. The attachment prong may also have a locking tab 37 extending radially outwards therefrom for engaging a portion of the hole in the shaft when the attachment prong is twisted in the hole.

With reference to FIG. 7, the attachment sleeve has a lumen 38 in communication with the open proximal end of the attachment sleeve. Optionally, the lumen of the attachment sleeve may have a resilient lining 39 with a plurality of inwardly radiating generally frusta-conical resilient retaining fins 40 frictionally engaging the one end of the writing instrument.

As to a further discussion of the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. A dental hygiene attachment system, comprising:
a tubular attachment sleeve having an open proximal end and a closed distal end;
said proximal end of said attachment sleeve being adapted for receiving therein one end of a writing instrument;
at least one dental tool having an elongate shaft portion and a head portion at a first end of said shaft portion of said dental tool;
said distal end of said attachment sleeve receiving therein a second end of said dental tool;
wherein said head portion of a first of said dental tools comprises a generally conical-shaped resilient deformable pick having an outwardly extending point;
wherein said head portion of a second of said dental tools comprises a toothbrush having a plurality of outwardly extending flexible bristles; and
wherein said head portion of a third of said dental tools comprises a generally C-shaped arcuate floss holder and a length of dental floss extending between opposing ends of said floss holder.

2. The dental hygiene attachment system of claim 1, wherein said distal end of said attachment sleeve has a generally oblong finger extent thereadjacent.

3. The dental hygiene attachment system of claim 1, wherein said distal end of said attachment sleeve has a bore therein which receives said second end of said shaft portion therein.

4. The dental hygiene attachment system of claim 3, wherein said shaft portion of said dental tool has a resiliently deformable annular retaining ring therearound positioned towards said second end of said shaft portion of said dental tool, said retaining ring of said shaft portion of said dental tool being inserted into said bore of said distal end of said attachment sleeve.

5. The dental hygiene attachment system of claim 1, wherein said pick of said first dental tool has an axis extending substantially perpendicular to said shaft portion of said first dental tool.

6. The dental hygiene attachment system of claim 1 wherein said head portion of said first dental tool has a bore therein receiving a resiliently deformable attachment extent of said pick of said first dental tool to detachably attach said pick to said head portion of said first dental tool.

7. The dental hygiene attachment system of claim 1, wherein said floss holder and said shaft portion of said third dental tool lie in a common plane with one another.

8. The dental hygiene attachment system of claim 1, wherein a cap is mounted to said distal end of said attachment sleeve and covers said dental tool therein.

9. A dental hygiene attachment system comprising:
a tubular attachment sleeve having an open proximal end and a closed distal end;
said proximal end of said attachment sleeve being adapted for receiving therein one end of a writing instrument;
at least one dental tool having an elongate shaft portion and a head portion at a first end of said shaft portion of said dental tool; and
said distal end of said attachment sleeve receiving therein a second end of said dental tool;
wherein a cap is mounted to said distal end of said attachment sleeve and covers said dental tool therein;
wherein said cap has an open end receiving said distal end of said attachment sleeve, wherein said attachment sleeve has a resilient attachment ridge therearound adjacent said distal end of said attachment sleeve, wherein said cap has an annular inner retaining groove adjacent said open end of said cap, and wherein said inner retaining groove receives therein said attachment ridge of said attachment sleeve to hold said cap on said distal end of said attachment sleeve.

10. A dental hygiene attachment system, comprising:
a writing instrument having at least one end;
wherein said writing instrument comprises a retractable ink pen having a depressible retraction actuating button outwardly extending from said one end of said writing instrument;

a dental hygiene attachment, comprising:
- a tubular attachment sleeve having an open proximal end and a closed distal end;
- said proximal end of said attachment sleeve receiving therein said one end of said writing instrument to attach said attachment sleeve to said one end of said writing instrument;
- wherein said distal end of said attachment sleeve has a generally oblong finger extent thereadjacent;
- at least one dental tool having an elongate shaft portion and a head portion at a first end of said shaft portion of said dental tool;
- said distal end of said attachment sleeve having a bore therein;
- said shaft portion of said dental tool having a second end opposite said first end of said dental tool, said second end of said shaft portion of said dental tool being inserted into said bore of said distal end of attachment sleeve;
- said shaft portion of said dental tool having a resiliently deformable annular retaining ring therearound positioned towards said second end of said shaft portion of said dental tool;
- said retaining ring of said shaft portion of said dental tool being inserted into said bore of said distal end of said attachment sleeve, said retaining ring being deformed in said bore to hold said second end of said shaft portion in said bore;
- wherein said head portion of a first of said dental tools comprises a generally conical-shaped resilient deformable pick having an outwardly extending point;
- said pick of said first dental tool having an axis extending substantially perpendicular to said shaft portion of said first dental tool;
- said head portion of said first dental tool having a bore therein receiving a resiliently deformable attachment extent of said pick of said first dental tool to detachably attach said pick to said head portion of said first dental tool;
- wherein said head portion of a second of said dental tools comprises a toothbrush having a plurality of outwardly extending flexible bristles;
- wherein said head portion of a third of said dental tools comprises a generally C-shaped arcuate floss holder and a length of dental floss extending between opposing ends of said floss holder;
- said floss holder and said shaft portion of said third dental tool lying in a common plane with one another;
- a cap being mounted to said distal end of said attachment sleeve and covering said dental tool therein;
- wherein said cap has an open end receiving said distal end of said attachment sleeve;
- said attachment sleeve having a resilient attachment ridge therearound adjacent said distal end of said attachment sleeve; and
- said cap having an annular inner retaining groove adjacent said open end of said cap, said inner retaining groove receiving therein said attachment ridge of said attachment sleeve to hold said cap on said distal end of said attachment sleeve.

11. The dental hygiene attachment system of claim 9, wherein said distal end of said attachment sleeve has a generally oblong finger extent thereadjacent.

12. The dental hygiene attachment system of claim 9, wherein said distal end of said attachment sleeve has a bore therein which receives said second end of said shaft portion therein.

13. The dental hygiene attachment system of claim 12, wherein said shaft portion of said dental tool has a resiliently deformable annular retaining ring therearound positioned towards said second end of said shaft portion of said dental tool, said retaining ring of said shaft portion of said dental tool being inserted into said bore of said distal end of said attachment sleeve.

14. The dental hygiene attachment system of claim 9, wherein said head portion of a first of said dental tools comprises a generally conical-shaped resilient deformable pick having an outwardly extending point.

15. The dental hygiene attachment system of claim 14, wherein said head portion of said first dental tool has a bore therein receiving a resiliently deformable attachment extent of said pick of said first dental tool to detachably attach said pick to said head portion of said first dental tool.

16. The dental hygiene attachment system of claim 14, wherein said head portion of a second of said dental tools comprises a toothbrush having a plurality of outwardly extending flexible bristles.

17. The dental hygiene attachment system of claim 16, wherein said head portion of a third of said dental tools comprises a generally C-shaped arcuate floss holder and a length of dental floss extending between opposing ends of said floss holder.

* * * * *